United States Patent
Berthier et al.

(10) Patent No.: US 10,632,443 B2
(45) Date of Patent: Apr. 28, 2020

(54) DELIVERY SYSTEM WITH IMPROVED DEPOSITION

(71) Applicant: Firmenich SA, Geneva (CH)

(72) Inventors: Damien Berthier, Geneva (CH); Geraldine Leon, Geneva (CH); Glenn Verhovnik, Geneva (CH)

(73) Assignee: Firmenich SA, Satigny (CH)

( * ) Notice: Subject to any disclaimer, the term of this patent is extended or adjusted under 35 U.S.C. 154(b) by 117 days.

(21) Appl. No.: 15/737,957

(22) PCT Filed: Jun. 28, 2016

(86) PCT No.: PCT/EP2016/064975
§ 371 (c)(1),
(2) Date: Dec. 19, 2017

(87) PCT Pub. No.: WO2017/001385
PCT Pub. Date: Jan. 5, 2017

(65) Prior Publication Data
US 2018/0178183 A1 Jun. 28, 2018

(30) Foreign Application Priority Data
Jun. 30, 2015 (EP) .................................. 15174539

(51) Int. Cl.
| | |
|---|---|
| *A61L 9/04* | (2006.01) |
| *A61K 8/00* | (2006.01) |
| *C11D 3/50* | (2006.01) |
| *B01J 13/22* | (2006.01) |
| *A61Q 13/00* | (2006.01) |
| *A61K 8/11* | (2006.01) |
| *A61K 8/73* | (2006.01) |
| *A61K 8/81* | (2006.01) |
| *A61K 8/84* | (2006.01) |
| *A61Q 5/02* | (2006.01) |
| *A61Q 5/12* | (2006.01) |

(52) U.S. Cl.
CPC ................ *B01J 13/22* (2013.01); *A61K 8/11* (2013.01); *A61K 8/737* (2013.01); *A61K 8/817* (2013.01); *A61K 8/8158* (2013.01); *A61K 8/84* (2013.01); *A61Q 5/02* (2013.01); *A61Q 5/12* (2013.01); *A61Q 13/00* (2013.01); *C11D 3/505* (2013.01); *A61K 2800/5426* (2013.01); *A61K 2800/56* (2013.01)

(58) Field of Classification Search
CPC .......... B01J 13/22; A61K 8/8158; A61K 8/22; A61K 8/95; A61K 8/737; A61K 8/817; A61K 2800/5426; A61K 2800/56; A61Q 13/00; A61Q 5/02; A61Q 5/12
USPC ......................................................... 512/4, 1
See application file for complete search history.

(56) References Cited

U.S. PATENT DOCUMENTS

| | | | |
|---|---|---|---|
| 2004/0071742 A1 | 4/2004 | Popplewell et al. | |
| 2006/0216509 A1 | 9/2006 | Kleban et al. | |
| 2007/0123442 A1* | 5/2007 | Holzner ................... | A61K 8/11 510/101 |
| 2009/0042759 A1 | 2/2009 | Brain et al. | |
| 2011/0237487 A1* | 9/2011 | Souter ................ | C11D 3/38609 510/374 |
| 2012/0148644 A1 | 6/2012 | Popplewell et al. | |
| 2014/0322283 A1* | 10/2014 | Berthier ................. | A61Q 13/00 424/401 |

FOREIGN PATENT DOCUMENTS

| | | |
|---|---|---|
| EP | 1407753 A1 | 4/2004 |
| EP | 2300146 B1 | 3/2017 |
| EP | 2579976 B1 | 8/2017 |
| WO | 2001041915 A1 | 6/2001 |
| WO | 2007004166 A1 | 1/2007 |
| WO | 2009153695 A1 | 12/2009 |
| WO | 2013068255 A1 | 5/2013 |

OTHER PUBLICATIONS

International Search Report and Written Opinion for international application No. PCT/EP2016/064975, dated Oct. 6, 2016.

* cited by examiner

*Primary Examiner* — Jessica Whiteley
(74) *Attorney, Agent, or Firm* — Armstrong Teasdale LLP

(57) ABSTRACT

The invention relates to microcapsules coated by a particular mixture of copolymers, which demonstrate a high rate of deposition when applied on a substrate. Those microcapsules can be used in several industries, in particular in perfumery and rinse-off applications. Perfuming compositions and perfumed consumer products comprising these microcapsules are also objects of the invention.

18 Claims, No Drawings

DELIVERY SYSTEM WITH IMPROVED DEPOSITION

RELATED APPLICATIONS

This application is a national stage application under 35 U.S.C. § 371 filing of International Patent Application PCT/EP2016/064975, filed Jun. 28, 2016, which claims the benefit of EP Application 15174539.5, filed Jun. 30, 2015. The contents of which are incorporated herein by reference in their entirety.

TECHNICAL FIELD

The invention relates to the field of delivery systems. More particularly, the invention concerns microcapsules coated with a particular mixture of copolymers, which demonstrate a high rate of deposition when applied on a substrate, therefore improving the delivery of an active ingredient encapsulated therein. Those microcapsules can be used in several industries, in particular in perfumery and rinse-off applications. Perfuming compositions and perfumed consumer products comprising these microcapsules are also objects of the invention.

BACKGROUND OF THE INVENTION

One of the problems faced by the perfumery industry lies in the relatively rapid loss of the olfactive benefit provided by odoriferous compounds due to their volatility, particularly that of "top-notes". This problem is generally tackled using a delivery system, e.g. capsules containing a perfume, to release the fragrance in a controlled manner.

In order to be successfully used in consumer products, perfume delivery systems must meet a certain number of criteria. The first requirement concerns stability in aggressive medium. In fact delivery systems may suffer from stability problems, in particular when incorporated into surfactant-based products such as detergents, wherein said systems tend to degrade and lose efficiency in the perfume-retention ability. It is also difficult to have a good stability and a good dispersion of the capsules altogether. The dispersion factor is very important because the aggregation of capsules increases the tendency of the capsule-containing product to phase separate, which represents an important disadvantage. On the other hand, perfume delivery systems must also perform during the actual use of the end-product by the consumer, in particular in terms of odor performance, as the perfume needs to be released when required. Another challenge faced by the perfumery industry is to provide delivery systems that are well deposited on the substrate for the treatment of which the end product is intended to be used, such as textile, skin, hair or other surfaces, so as to possibly remain on the substrate even after a rinsing step. To address this last specific problem, the use of cationic capsules has been described in the prior art. Cationic capsules are also known to be better dispersed in several applications.

For example, WO 01/41915 discloses a process for the preparation of capsules carrying cationic charges. Such a process is allegedly applicable to a large variety of microcapsules, in particular polyurethane-polyurea microcapsules are mentioned. After their formation, the capsules are placed in a medium which is favourable for the treatment with cationic polymers. The treatment with cationic polymers is carried out after purification of the basic capsule slurry, in order to eliminate anionic or neutral polymers which were not incorporated in the capsule wall during formation thereof, and other free electrically charged compounds involved in the encapsulation process. In particular, the capsules are diluted, isolated and then re-suspended in water, or even washed to further eliminate anionic compounds. After the purification step, the capsules are agitated vigorously and the cationic polymers are added. Partially quaternized copolymers of polyvinylpyrrolidones are cited to this purpose, among many other suitable polymers. The described process comprises several steps following the capsule formation, said process being therefore time consuming and not economically profitable.

US 2006/0216509 also discloses a process to render polyurea capsules positively-charged. This process involves the addition, during the wall formation, of polyamines, the capsules thus bearing latent charges, depending on the pH of the medium. Once formed, the capsules are subsequently cationized by acid action or alkylation to bear permanent positive charges. The cationic compounds therefore react with the capsule wall, chemically changing the latter.

WO2009/153695 from the applicant discloses a simplified process for the preparation of polyurea microcapsules bearing permanent positive charges based on the use of a specific stabilizer and which present good deposition on a substrate.

Deposition aids have also been described in prior arts in association with other types of capsules than polyurea-based ones. For instance WO2013/068255 relating to formaldehyde-free aminoplast-based microcapsules discloses in the process for the preparation of the microcapsules the option to add to the microcapsule dispersion a cationic polymer to improve deposition.

Despite those prior disclosures, there is still a need to improve the ability of delivery systems to deposit on a substrate and to adhere on the substrate in particular in the perfumery industry for leave-on applications and rinse-off applications, while being always performing in terms of perfume release and stability.

The microcapsules of the invention solve this problem as they proved to show improvement in terms of deposition properties compared to deposition aids disclosed heretofore.

The present invention provides new microcapsules for delivering an encapsulated material such as a perfume and/or other hydrophobic materials, which are coated with a particular composition of cationic copolymers.

SUMMARY OF THE INVENTION

A first object of the present invention relates to a core-shell microcapsule slurry comprising microcapsules having an oil-based core and a polymeric shell coated with a composition comprising at least a first cationic copolymer and a second cationic polymer, characterized in that the weight ratio between the first copolymer and the second copolymer in the slurry is comprised between 0.05 and 7, preferably between 0.5 and 6.5, more preferably between 1 and 6.2, even more preferably between 3 and 6, wherein the first cationic copolymer comprises acrylamidopropyltrimonium chloride.

The invention also relates to a microcapsule powder obtained by drying the microcapsule slurry as defined above.

The invention also relates to a process for the preparation of a core-shell microcapsule slurry, comprising the step of adding to an aqueous dispersion of un-coated microcapsules, a composition comprising at least a first cationic copolymer and a second cationic copolymer wherein the weight ratio between the first and second copolymer is comprised between 0.05 and 7, preferably between 0.5 and 6.5, more preferably between 1 and 6.2, even more preferably between 3 and 6, wherein the first cationic copolymer comprises acrylamidopropyltrimonium chloride.

Another object of the invention is a perfuming composition comprising microcapsule slurry or microcapsule powder as defined above, wherein the core comprises a perfume; at least one ingredient selected from the group consisting of a perfumery carrier, a perfuming co-ingredient and mixtures thereof; and optionally a perfumery adjuvant.

Another object of the invention is a consumer product in the form of a home- or personal-care product that includes a perfume composition as described herein.

Another object of the invention is a shampoo or hair conditioner composition comprising
(i) from 1 to 50 wt % of surfactant
(ii) from 0.05 to 10 wt % of free perfume oil
(iii) from 0.05 to 10 wt % of an organic acid
(iv) from 0.2 to 0.8 wt % of a microcapsule slurry obtainable by the process defined above.

Yet another embodiment of the invention is a method for depositing microcapsules on a substrate which comprises treating said substrate with a perfume composition disclosed herein.

Finally, another object of the invention is the use of a composition as defined above for depositing microcapsules on a substrate.

DETAILED DESCRIPTION OF THE INVENTION

Unless stated otherwise, percentages (%) are meant to designate a percentage by weight of a composition.

The present invention now has determined a way to improve the efficiency in depositing microcapsules on a substrate. What is referred to as improving deposition or improving deposition efficiency is the percentage of microcapsules that remains on a substrate during use, in particular that remains on a substrate after a rinsing step. Better deposition translates then into an improvement in the delivery performance of the active ingredient encapsulated, for instance the olfactive performance in the case of a perfume, meaning that the microcapsules are able to deliver long lasting perception of a fragrance. It has been surprisingly found that while cationic polymers were widely known as deposition aids for microcapsules, specific compositions containing at least two different cationic polymers present in specific ratios, could significantly improve the performance of those microcapsules in terms of deposition and long lasting effect of the active ingredient encapsulated therein.

What is meant by "different" cationic polymers in the context of the invention is cationic polymers differing from a charge density standpoint, a molecular weight standpoint and/or with different monomer ratios.

A first object of the present invention therefore consists of a core-shell microcapsule slurry comprising microcapsules having an oil-based core and a polymeric shell coated with a composition comprising at least a first cationic copolymer and a second cationic polymer, characterized in that the weight ratio between the first copolymer and the second copolymer in the slurry is comprised between 0.05 and 7, preferably between 0.5 and 6.5, more preferably between 1 and 6.2, even more preferably between 3 and 6, wherein the first cationic copolymer comprises acrylamidopropyltrimonium chloride.

The particular composition of cationic polymers coating the microcapsule according to the invention has shown to improve the deposition efficiency from the capsule onto a substrate compared to what was achieved heretofore with single cationic polymers, and consequently provides an advantage in terms of long lasting delivery of the active ingredient present in the core of the microcapsule. The microcapsule according to the invention is preferably anionic.

According to a preferred embodiment, the second copolymer is selected from the group consisting of cationic polymers based on acrylamide, methacrylamide, N-vinylpyrrolidone, quaternized N,N-dimethylaminomethacrylate, diallyldimethylammonium chloride, quaternized vinylimidazole (3-methyl-1-vinyl-1H-imidazol-3-ium chloride), vinylpyrrolidone, cassia hydroxypropyltrimonium chloride, guar hydroxypropyltrimonium chloride or polygalactomannan 2-hydroxypropyltrimethylammonium chloride ether, starch hydroxypropyltrimonium chloride and cellulose hydroxypropyltrimonium chloride and mixtures thereof.

More preferably, the second copolymer is selected from the group consisting of polyquaternium-5, polyquaternium-6, polyquaternium-7, polyquaternium10, polyquaternium-11, polyquaternium-16, polyquaternium-22, polyquaternium-28, polyquaternium-43, polyquaternium-44, polyquaternium-46, cassia hydroxypropyltrimonium chloride, guar hydroxypropyltrimonium chloride or polygalactomannan 2-hydroxypropyltrimethylammonium chloride ether, starch hydroxypropyltrimonium chloride and cellulose hydroxypropyltrimonium chloride and mixtures thereof.

According to a particular embodiment, the first cationic copolymer consists of poly(acrylamidopropyltrimonium chloride-co-acrylamide).

In the present invention "poly(acrylamidopropyltrimonium chloride-co-acrylamide" and "acrylamidopropyltrimonium chloride/acrylamide copolymer" are used indifferently.

According to an embodiment, the first cationic copolymer comprises acrylamidopropyltrimonium chloride, preferably consists of poly(acrylamidopropyltrimonium chloride-co-acrylamide and the second copolymer is selected from the group consisting of cationic polyacrylamide, polyquaternium-7, polyquaternium-16, cationic starch, cassia hydroxypropyltrimonium chloride, cationic cellulose and cationic polygalactomannan and mixtures thereof. Preferably, the first cationic copolymer comprises acrylamidopropyltrimonium chloride, preferably consists of poly(acrylamidopropyltrimonium chloride-co-acrylamide and the second copolymer is selected from the group consisting of polyquaternium-16, polyquaternium-7, cassia hydroxypropyltrimonium chloride.

The core-shell microcapsule according to the invention comprises an oil-based core. By "oil", it is meant an organic phase that is liquid at about 20° C. which forms the core of the core-shell capsules. According to any one of the invention embodiments, said oil comprises an ingredient or composition selected amongst a perfume, perfume ingredient, flavour, flavour ingredient, nutraceuticals, cosmetic ingredient, sunscreen agent, insecticide, malodour counteracting substance, bactericide, fungicide, biocide actives, insect repellent or attractant, insect control agent, drug, agrochemical ingredient and mixtures thereof.

According to a particular embodiment, said oil-based core comprises a perfume with another ingredient selected from the group consisting of nutraceuticals, cosmetics, insect control agents and biocide actives.

According to a particular embodiment, the oil-based core comprises a perfume or flavour. According to a preferred embodiment, the oil-based core comprises a perfume. According to another embodiment, the oil-based core consists of a perfume.

By "perfume oil" (or also "perfume") what is meant here is an ingredient or composition that is a liquid at about 20° C. According to any one of the above embodiments said perfume oil can be a perfuming ingredient alone or a mixture of ingredients in the form of a perfuming composition. As a "perfuming ingredient" it is meant here a compound, which is used for the primary purpose of conferring or modulating an odour. In other words such an ingredient, to be considered as being a perfuming one, must be recognized by a person skilled in the art as being able to at least impart or modify in a positive or pleasant way the odor of a composition, and not just as having an odor. For the purpose of the present invention, perfume oil also includes combination of perfuming ingredients with substances which together improve, enhance or modify the delivery of the perfuming ingredients, such as perfume precursors, emulsions or dispersions, as well as combinations which impart an additional benefit beyond that of modifying or imparting an odor, such as long-lasting, blooming, malodour counteraction, antimicrobial effect, microbial stability, insect control.

The nature and type of the perfuming ingredients present in the oil phase do not warrant a more detailed description here, which in any case would not be exhaustive, the skilled person being able to select them on the basis of its general knowledge and according to intended use or application and the desired organoleptic effect. In general terms, these perfuming ingredients belong to chemical classes as varied as alcohols, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said ingredients may also be compounds known to release in a controlled manner various types of perfuming compounds.

The perfuming ingredients may be dissolved in a solvent of current use in the perfume industry. The solvent is preferably not an alcohol. Examples of such solvents are diethyl phthalate, isopropyl myristate, Abalyn® (rosin resins, available from Eastman), benzyl benzoate, ethyl citrate, limonene or other terpenes, or isoparaffins. Preferably, the solvent is very hydrophobic and highly sterically hindered, like for example Abalyn® or benzyl benzoate. Preferably the perfume comprises less than 30% of solvent. More preferably the perfume comprises less than 20% and even more preferably less than 10% of solvent, all these percentages being defined by weight relative to the total weight of the perfume. Most preferably, the perfume is essentially free of solvent.

The nature of the polymeric shell from the microcapsules of the invention can vary. As non-limiting examples, the shell can be aminoplast-based, polyurea-based or polyurethane-based. The shell can also be hybrid, namely organic-inorganic such as a hybrid shell composed of at least two types of inorganic particles that are cross-linked, or yet a shell resulting from the hydrolysis and condensation reaction of a polyalkoxysilane macro-monomeric composition.

According to a particular embodiment, the shell comprises an aminoplast copolymer, such as melamine-formaldehyde or urea-formaldehyde or cross-linked melamine formaldehyde or melamine glyoxal.

According to another embodiment the shell is polyurea-based made from, for example but not limited to isocyanate-based monomers and amine-containing crosslinkers such as guanidine carbonate and/or guanazole. Preferred polyurea microcapsules comprise a polyurea wall which is the reaction product of the polymerisation between at least one polyisocyanate comprising at least two isocyanate functional groups and at least one reactant selected from the group consisting of a water soluble guanidine salt and guanidine; a colloidal stabilizer or emulsifier; and an encapsulated perfume. According to a particular embodiment the colloidal stabilizer includes an aqueous solution of between 0.1% and 0.4% of polyvinyl alcohol, between 0.6% and 1% of a cationic copolymer of vinylpyrrolidone and of a quaternized vinylimidazol (all percentages being defined by weight relative to the total weight of the colloidal stabilizer). According to another embodiment, the emulsifier is an anionic or amphiphilic biopolymer preferably chosen from the group consisting of gum Arabic, soy protein, gelatin, sodium caseinate and mixtures thereof.

According to another embodiment, the shell is polyurethane-based made from, for example but not limited to polyisocyanate and polyols, polyamide, polyester, etc.

Another object of the present invention is a microcapsule powder obtained by drying the microcapsule slurry of the present invention.

Any drying method known to a skilled person in the art can be used; in particular the slurry may be spray-dried preferably in the presence of a polymeric carrier material such as polyvinyl acetate, polyvinyl alcohol, dextrines, natural or modified starch, vegetable gums, pectins, xanthanes, alginates, carragenans or cellulose derivatives to provide microcapsules in a powder form.

Another object of the present invention consists of a process for the preparation of a core-shell microcapsule slurry as defined above, comprising the step of adding to an aqueous dispersion of core-shell un-coated microcapsules, a composition comprising at least a first cationic copolymer and a second cationic copolymer wherein the weight ratio between the first and the second copolymer is comprised between 0.05 and 7, preferably between 0.5 and 6.5, more preferably between 1 and 6.2, even more preferably between 3 and 6, wherein the first cationic copolymer comprises acrylamidopropyltrimonium chloride.

According to a particular embodiment, the first cationic copolymer consists of poly(acrylamidopropyltrimonium chloride-co-acrylamide).

The preparation of an aqueous dispersion/slurry of core-shell microcapsules is well known by a skilled person in the art. In one aspect, said microcapsule wall material may comprise any suitable resin and especially including melamine, glyoxal, polyurea, polyurethane, polyamide, polyester, etc. Suitable resins include the reaction product of an aldehyde and an amine, suitable aldehydes include, formaldehyde and glyoxal. Suitable amines include melamine, urea, benzoguanamine, glycoluril, and mixtures thereof. Suitable melamines include, methylol melamine, methylated methylol melamine, imino melamine and mixtures thereof. Suitable ureas include, dimethylol urea, methylated dimethylol urea, urea-resorcinol, and mixtures thereof. Suitable materials for making may be obtained from one or more of the following companies Solutia Inc. (St Louis, Mo. U.S.A.), Cytec Industries (West Paterson, N.J. U.S.A.), Sigma-Aldrich (St. Louis, Mo. U.S.A.).

According to a particular embodiment, the core-shell microcapsule is a formaldehyde-free capsule. A typical process for the preparation of aminoplast formaldehyde-free microcapsules slurry comprises the steps of 1) preparing an oligomeric composition comprising the reaction product of, or obtainable by reacting together
   a) a polyamine component in the form of melamine or of a mixture of melamine and at least one $C_1$-$C_4$ compound comprising two $NH_2$ functional groups;
   b) an aldehyde component in the form of a mixture of glyoxal, a $C_{4-6}$ 2,2-dialkoxy-ethanal and optionally a glyoxalate, said mixture having a molar ratio glyoxal/$C_{4-6}$ 2,2-dialkoxy-ethanal comprised between 1/1 and 10/1; and
   c) a protic acid catalyst;
2) preparing an oil-in-water dispersion, wherein the droplet size is comprised between 1 and 600 um, and comprising:
   i. an oil;
   ii. a water medium
   iii. at least an oligomeric composition as obtained in step 1;
   iv. at least a cross-linker selected amongst
   A) $C_4$-$C_{12}$ aromatic or aliphatic di- or tri-isocyanates and their biurets, triurets, trimmers, trimethylol propane-adduct and mixtures thereof; and/or
   B) a di- or tri-oxiran compounds of formula

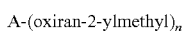

wherein n stands for 2 or 3 and 1 represents a $C_2$-$C_6$ group optionally comprising from 2 to 6 nitrogen and/or oxygen atoms;
   v. optionally a $C_1$-$C_4$ compounds comprising two $NH_2$ functional groups;
3) Heating said dispersion;
4) Cooling said dispersion.

This process is described in more details in WO 2013/068255, the content of which is included by reference.

According to another embodiment, the shell of the microcapsule is polyurea- or polyurethane-based. Examples of processes for the preparation of polyurea and polyureathane-based microcapsule slurry are for instance described in WO2007/004166, EP 2300146, EP2579976 the contents of which is also included by reference. Typically a process for the preparation of polyurea or polyurethane-based microcapsule slurry include the following steps:
a) Dissolving at least one polyisocyanate having at least two isocyanate groups in an oil to form an oil phase;
b) Preparing an aqueous solution of an emulsifier or colloidal stabilizer to form a water phase;
c) Adding the oil phase to the water phase to form an oil-in-water dispersion, wherein the mean droplet size is comprised between 1 and 500 μm, preferably between 5 and 50 μm;
d) Applying conditions sufficient to induce interfacial polymerisation and form microcapsules in form of a slurry.

Microcapsules of the type hereinabove described are manufactured in the form of an aqueous slurry, having typically 20 to 50% solids content, and more typically 30 to 45% solid content, where the term "solids content" refers to the total weight of the microcapsules. The slurry may contain formulation aids, such as stabilizing and viscosity control hydrocolloids, biocides, and additional formaldehyde scavengers.

The composition resulting from this manufacturing process is a slurry. The slurry comprises microcapsules, water and precursor materials for making the microcapsules.

According to an embodiment, the process comprises a further step consisting of drying the microcapsule slurry to obtain a microcapsule powder.

Any drying method known to a skilled person in the art can be used; in particular the slurry may be spray-dried preferably in the presence of a polymeric carrier material such as polyvinyl acetate, polyvinyl alcohol, dextrines, natural or modified starch, vegetable gums, pectins, xanthanes, alginates, carragenans or cellulose derivatives to provide microcapsules in a powder form.

The slurry may comprise other minor ingredients, such as an activator for the polymerization process and/or a pH buffer. To the slurry, a formaldehyde scavenger may be added.

According to a preferred embodiment, the composition of the first cationic copolymer and the second cationic copolymer is added in an amount such that the total concentration of cationic copolymers is comprised between 0.3 and 1.5 wt % of the slurry, preferably between 0.5 and 1.0%, most preferably between 0.6 and 0.9 wt %.

According to a particular embodiment, the first cationic copolymer is present at a concentration comprised between 0.3 and 0.9 wt % of the microcapsule slurry, preferably between 0.4 and 0.7 wt %, most preferably between 0.5 and 0.65 wt %.

According to a particular embodiment, the second cationic copolymer is present at a concentration comprised between 0.01 and 0.9 wt % of the microcapsule slurry, preferably between 0.05 and 0.7 wt %, most preferably between 0.07 and 0.25 wt %.

A microcapsule slurry obtainable by a process according to any of the above embodiments is also an object of the present invention.

The microcapsules of the invention described herein can, when the core includes a perfume, be used as perfuming ingredients in consumer products of the home- or personal-care type.

A further object of the present invention is a perfuming composition comprising
(i) microcapsule slurry or microcapsule powder as defined above, wherein the oil comprises a perfume;
(ii) at least one ingredient selected from the group consisting of a perfumery carrier and a perfuming co-ingredient, and
(iii) optionally a perfumery adjuvant.

As liquid perfumery carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery co-ingredient, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company). By "perfumery co-ingredient" it is meant here a compound, which is used in a perfuming preparation or a composition to impart a hedonic effect or modulate the overall odour and which is not a microcapsule as defined above. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the perfuming composition do not warrant a more detailed description here, which in any case would not be exhaustive, the skilled person being able to select them on the basis of his general knowledge and according to the intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

Preferably, the perfuming composition according to the invention comprises between 0.1 and 30% by weight of microcapsule slurry or microcapsule powder as defined above.

The invention's microcapsules can advantageously be used in all the fields of modern perfumery, i.e. fine or functional perfumery. Consequently, another object of the present invention is represented by a perfuming consumer product comprising as a perfuming ingredient, the microcapsules defined above or a perfuming composition as defined above.

The invention's microcapsules can therefore be added as such or as part of an invention's perfuming composition in a perfuming consumer product.

For the sake of clarity, it has to be mentioned that, by "perfuming consumer product" it is meant a consumer product which is expected to deliver at least a pleasant perfuming effect to the surface to which it is applied (e.g. skin, hair, textile, or home surface). In other words, a perfuming consumer product according to the invention is a perfumed consumer product which comprises a functional formulation, as well as optionally additional benefit agents, corresponding to the desired consumer product, e.g. a detergent or an air freshener, and an olfactive effective amount of at least one invention's compound.

The nature and type of the constituents of the perfumery consumer product do not warrant a more detailed description here, which in any case would not be exhaustive, the skilled person being able to select them on the basis of his general knowledge and according to the nature and the desired effect of said product. Formulations of consumer products in which the microcapsules of the invention can be incorporated can be found in the abundant literature relative to such products. These formulations do not warrant a detailed description here which would in any case not be exhaustive.

The person skilled in the art of formulating such consumer products is perfectly able to select the suitable components on the basis of his general knowledge and of the available literature.

In particular, examples of such formulations can be found in handbooks such as for example Handbook of detergents; CTFA Cosmetic ingredient handbook, $10^{th}$ edition or more recent versions; Formulating detergents and personal care products: a guide to product development (2000); Cosmetic formulation of skin care products (2006) as well as in the abundant patent literature in the field of body care and home care consumer products.

Non-limiting examples of suitable perfumery consumer product include a perfume, such as a fine perfume, a cologne or an after-shave lotion; a fabric care product, such as a liquid or solid detergent, tablets and pods, a fabric softener, a dryer sheet, a fabric refresher, an ironing water, or a bleach; a body-care product, such as a hair care product (e.g. a shampoo, leave-on or rinse-off hair conditioner, styling product, dry shampoo, a colouring preparation or a hair spray), a cosmetic preparation (e.g. a vanishing cream, body lotion or a deodorant or antiperspirant), or a skin-care product (e.g. a perfumed soap, shower or bath mousse, body wash, oil or gel, bath salts, shave gel or foam, cleansing wipes or a hygiene product); an air care product, such as an air freshener or a "ready to use" powdered air freshener; or a home care product, such all-purpose cleaners, liquid or power or tablet dishwashing products, toilet cleaners or products for cleaning various surfaces, for example sprays & wipes intended for the treatment/refreshment of textiles or hard surfaces (floors, tiles, stone-floors, etc).

According to a preferred embodiment, the consumer product is a shampoo or a rinse-off conditioner comprising (i) from 1 to 50 wt % of surfactant (ii) from 0.05 to 10 wt % of free perfume oil (iii) from 0.05 to 10 wt % of an organic acid (iv) from 0.2 to 0.8 wt % of a microcapsule slurry as defined above.

According to another preferred embodiment, the product is a perfumed soap. According to another preferred embodiment, the product is a body wash.

Preferably, the consumer product comprises from 0.1 to 15 wt %, more preferably between 0.2 and 5 wt % of the microcapsules of the present invention, these percentages being defined by weight relative to the total weight of the consumer product. Of course the above concentrations may be adapted according to the olfactive effect desired in each product.

The capsules of the invention have proven to be particularly useful in rinse-off application as their deposition is much superior to delivery systems known heretofore.

The performance of the microcapsules object of the present invention can be determined by olfactive evaluations and measurements (see Example 1-4), as well as by measure of deposition % (see Examples 5 and 6).

The invention will now be further described by way of examples. It will be appreciated that the invention as claimed is not intended to be limited in any way by these examples.

EXAMPLES

Example 1

Preparation of Microcapsules According to the Present Invention

General Procedure

In a round bottom flask, melamine (0.91 g), 2,2-dimethoxyethanal (60 wt % in water, 1.37 g), glyoxal (40 wt % in water, 1.73 g) and 2-oxoacetic acid (50 wt % in water, 0.58 g) were dispersed in water (1.48 g) at RT. The pH value of the dispersion was controlled with sodium hydroxide (30 wt % in water, pH=9.5). The reaction mixture was heated at 45° C. for 25 minutes to give a solution. Then water (6.31 g) was added and the resin was stirred at 45° C. for 5 min.

Resin was transferred in a 200 mL beaker. Guanazole (0.60 g) was dissolved in a solution of Ambergum 1221 (2 wt % in water, 27.04 g). The resulting solution was introduced into the beaker. A solution of Takenate D-110N (2.15 g), perfume (28.06 g) and Uvinul A plus (1.40 g) was added into the aqueous solution. The biphasic reaction mixture was sheared with an Ultra-turrax at 21500 rpm for 2 min. Acetic acid was added to initiate the polycondensation (pH=5.35). The quality of the emulsion was controlled by light microscopy. The emulsion was transferred into a 200 mL Schmizo reactor and was heat at 45° C. for 1 h, then at 60° C. for 1 h and finally at 80° C. for 2 h. A solution of first cationic copolymer namely acrylamidopropyltrimonium chloride/acrylamide copolymer (Salcare® 60, origin BASF) (20 g, 3 wt % in water), and second cationic copolymer such as polyquaternium-16 (Luviquat® FC550, origin BASF, Germany) (1 wt % in water), was then added and the reaction mixture was heat at 80° C. for 30 min. A solution of urea (6.25 g, 50 wt % in water) was finally added to the reaction mixture, which was heat at 80° C. for 30 min.

TABLE 1

| Perfume oil composition | |
| --- | --- |
| Raw material | Amount (g) |
| Romascone ®[1] | 10.0 |
| Verdox ®[2] | 10.0 |
| Lorysia ®[3] | 10.0 |
| Salicynile[4] | 10.0 |
| Cyclosal[5] | 10.0 |

[1] methyl 2,2-dimethyl-6-methylene-1-cyclohexanecarboxylate; origin and trademark from Firmenich SA, Geneva, Switzerland
[2] 2-tert-butyl-1-cyclohexyl acetate; origin and trademark from International Flavors & Fragrances, USA
[3] 4-(1,1-dimethylethyl)-1-cyclohexyl acetate; origin and trademark from Firmenich SA, Geneva, Switzerland
[4] (2Z)-2-phenyl-2-hexenenitrile; origin: Firmenich SA, Geneva, Switzerland
[5] (+−)-3-(4-isopropylphenyl)-2-methylpropanal; origin: Firmenich SA, Geneva, Switzerland Four different microcapsule slurries were prepared with different concentrations of second cationic copolymer, as detailed in Table 2.

Solutions of different cationic copolymers were added to poly(acrylamidopropyltrimonium chloride-co-acrylamide) (Salcare® SC60, used as a solution at 3 wt %) to afford microcapsules A-1 to D-10 of the present invention according to the protocol described above (Table 2).

Capsules were prepared with polyquaternium 16 (Luviquat® FC550; origin: BASF); polygalactomannan 2-hydroxy propyltrimethylammonium chloride ether (Jaguar C13S or Jaguar C17AD; origin: Rhodia), polyquaternium-7 (Merquat 550; origin: BASF), polyquarternium-11 (Luviquat® PQ11; origin: BASF), or polyquarternium-16 (Luviquat® Style, FC370 or Excellence; origin: BASF). All copolymers were used as aqueous solutions at 1 wt %.

TABLE 2

Composition of cationic copolymer solutions from capsules A-1 to D-10

| Capsules | Jaguar C13S | Jaguar C17AD | Merquat 550 | Luviquat® PQ11 | Luviquat® Style | Luviquat® FC370 | Luviquat® Excellence | Luviquat® EC550 |
| --- | --- | --- | --- | --- | --- | --- | --- | --- |
| A-1 | | | | | | | | 11 g |
| B-1 | | | | | | | | 22 g |
| C-1 | | | | | | | | 44 g |
| D-1 | | | | | | | | 66 g |
| A-2 | 11 g | | | | | | | |
| B-2 | 22 g | | | | | | | |
| C-2 | 44 g | | | | | | | |
| D-2 | 66 g | | | | | | | |
| A-3 | | 11 g | | | | | | |
| B-3 | | 22 g | | | | | | |
| C-3 | | 44 g | | | | | | |
| D-3 | | 66 g | | | | | | |
| A-4 | | | 11 g | | | | | |
| B-4 | | | 22 g | | | | | |
| C-4 | | | 44 g | | | | | |
| D-4 | | | 66 g | | | | | |
| A-7 | | | | 11 g | | | | |
| B-7 | | | | 22 g | | | | |
| C-7 | | | | 44 g | | | | |
| D-7 | | | | 66 g | | | | |
| A-8 | | | | | 11 g | | | |
| B-8 | | | | | 22 g | | | |
| C-8 | | | | | 44 g | | | |
| D-8 | | | | | 66 g | | | |
| A-9 | | | | | | 11 g | | |
| B-9 | | | | | | 22 g | | |
| C-9 | | | | | | 44 g | | |
| D-9 | | | | | | 66 g | | |
| A-10 | | | | | | | 11 g | |
| B-10 | | | | | | | 22 g | |

TABLE 2-continued

Composition of cationic copolymer solutions from capsules A-1 to D-10

| Capsules | Jaguar C13S | Jaguar C17AD | Merquat 550 | Luviquat ® PQ11 | Luviquat ® Style | Luviquat ® FC370 | Luviquat ® Excellence | Luviquat ® EC550 |
|---|---|---|---|---|---|---|---|---|
| C-10 | | | | | | | 44 g | |
| D-10 | | | | | | | 66 g | |

Three other different microcapsule slurries were prepared with perfume D (see table 3) according to the protocol described above.
Solutions of different cationic copolymers were added to poly(acrylamidopropyltrimonium chloride-co-acrylamide) (Salcare® SC60, used as a solution at 3 wt %) to afford microcapsules E, F and H (see table 4).
The final concentrations of the first copolymer (poly(acrylamidopropyltrimonium chloride-co-acrylamide—Salcare® SC60) and of the second copolymers in the slurry are 0.62 and 0.10 wt %, respectively.

TABLE 3

Composition of perfume D

| Raw Mat | % in oil |
|---|---|
| Ethyl 2-methyl-pentanoate | 4.00% |
| 2,4-Dimethyl-3-cyclohexene-1-carbaldehyde | 4.00% |
| Allyl Heptanoate | 6.60% |
| (Z)-3-hexen-1-ol Butyrate | 1.30% |
| Allyl amyl glycolate | 13.10% |
| Delta Damascone | 2.00% |
| Verdyl acetate | 24.30% |
| Methylnaphtylcetone | 1.30% |
| Hedione ®[3] | 6.60% |
| Iso E Super ®[4] | 19.70% |
| Ald. Hexylcinnamique | 13.10% |
| Habanolide ®[5] | 4.00% |
| Total | 100% |

[3]Trademark from Firmenich; Methyl-cis-3-oxo-2-pentyl-1-cyclopentane acetate, origin: Firmenich SA, Geneva, Switzerland
[4]Trademark from IFF; 7-acetyl,1,2,3,4,5,6,7,8-octahydro-1,1,6,7-tetramethyl naphthalene
[5]Trademark from Firmenich; pentadecenolide, origin: Firmenich SA, Geneva, Switzerland

TABLE 4

Composition of cationic copolymer in capsules E, F and H

| | First copolymer | Second copolymer | | |
|---|---|---|---|---|
| Capsules | Poly(acrylamidopropyltrimonium chloride-co-acrylamide)[1] | Polyquaternium-16[2] | Polyquaternium-7[3] | Polyquatermium 16[4] |
| E | 20 g | 1 g | | |
| F | 20 g | | 1.1 g | |
| H | 20 g | | | 1 g |

[1]Salcare ® SC60 Trademark from BASF
[2]Luviquat ® FC550 Trademark from BASF
[3]Merquat 550 Trademark from Merck & Co
[4]Luviquat ® Style Trademark from BASF Example 2

Preparation of Control Microcapsules
Capsules were prepared as described in Example 1 with only poly(acrylamidopropyltrimonium chloride-co-acrylamide) (Salcare® SC60). After the addition of urea, the dispersion was cooled down RT before the addition of xanthan gum (0.4 g).

TABLE 5

Quantity of poly(acrylamidopropyltrimonium chloride-co-acrylamide) (Salcare ® SC60) solution in control microcapsules

| Ingredients | Comparative capsule A | Comparative capsule B |
|---|---|---|
| poly(acrylamidopropyltrimonium chloride-co-acrylamide)[1] | 20 g | 29 g |

[1]Salcare SC60

Comparative capsules C—H were prepared as described in Example 1 with perfume D with different single cationic polymers. After the addition of urea, the dispersion was cooled down RT before the addition of xanthan gum (0.4 g) (see table 6 below).

TABLE 6

Quantity of single cationinc copolymers in control microcapsules

| Comparative capsules | Single cationic copolymer | Concentration [wt %] |
|---|---|---|
| C | poly (acrylamidopropyltrimonium chloride-co-acrylamide)[1] | 0.84 |
| E | Polyquaternium-16[2] | 1.07 |
| F1 | Polyquaternium-7[3] | 1.07 |
| F2 | Polyquaternium-7[3] | 0.54 |
| H | Polyquatermium 16[4] | 0.79 |

[1]Salcare ® SC60 Trademark from BASF
[2]Luviquat ® FC550 Trademark from BASF
[3]Merquat 550 Trademark from Merck & Co
[4]Luviquat ® Style Trademark from BASF Example 3

Application in Shampoo of Capsules Prepared with 0.6% poly(acrylamidopropyltrimonium chloride-co-acrylamide) (Salcare® SC60)
A model shampoo base (Table 7) was prepared to test the capsules on hair (Table 7).

TABLE 7

Composition of transparent shampoo base

| Step | Product | Description | Concentration [wt %] |
|---|---|---|---|
| A | Water | | 44.4 |
| | Ucare Polymer JR-400 | Polyquaternium-10 | 0.3 |
| | Glycerin 85% | | 1.0 |
| | Glydant | DMDM Hydantoin | 0.2 |
| B | Texapon NSO IS | Sodium Laureth Sulfate | 28.0 |
| | Tego Betain F 50 | Cocamidopropyl Betaine | 3.2 |
| | Amphotensid GB 2009 | Disodium Cocoamphodiacetate | 2.0 |
| C | Texapon NSO IS | Sodium Laureth Sulfate | 4.0 |
| | Monomuls 90 L-12 | Glyceryl Laureate | 0.3 |
| D | Water deionised | | 1.0 |
| | Nipagin Monosodium | Sodium Methylparaben | 0.1 |
| E | Sodium Chloride 10% aq. | | 15.0 |
| | Perfume | | 0.5 |
| | Total | | 100 |

Formulation and evaluation on hair.

Capsules were incorporated at a dosage corresponding to 0.2% of perfume in the shampoo base and macerated at room temperature for at least 24 hours. Two dry hair swatches (10 g, Kerling Int., Cat. No.: 826500, Euro-Natural hair) were wet for 30 s under warm water (about 37° C.) and then were washed with 1 g of shampoo per 10 g of hair for 30 s. with gentle rubbing between the fingers. The washed hair swatches were rinsed in one 1 L beaker previously filled with warm water. They were dipped into the beaker three times (three times in, three times out). Then they were dipped into the beaker and slowly moved back and forth three times in each direction, and finally rinsed for 30 s. (15 s. on each side) under running water (flow rate 4 L/min) without touching the swatches at all. Excess of water was removed by squeezing of the swatch from the plastic part at the top to the end of the hair. Hair swatches were not touched anymore or squeezed out to remove excess water. A second wash with 1 g of shampoo for 30 s. was done and the above rinsing protocol was repeated. Hair swatches were put on the drying rack to air dry at room temperature for 24 hours.

Fragrance intensity of the hair swatches was evaluated before combing the hair according to the following perfume intensity scale: 1-Imperceptible, 2-Slightly perceptible, 3-Weak, 4-Medium, 5-Sustained, 6-Intense, 7-Very intense. Hair swatches were combed three times with the thin part of the comb. Perfume intensity just after combing the hair was evaluated according to the same scale. Once a hair swatch was touched, rubbed or combed, it could not be evaluated again for the "before combing" step. Thus at least two sets of hair swatches were prepared. One was never combed and used only for the "before combing" step. The other set was combed by a maximum of ten panelists for the "after combing" step. If more than ten panelists were required, another set of hair swatches was prepared for the "after combing" step. Throughout the washing protocol, hands were protected by gloves.

TABLE 8

Perfume intensity from microcapsules containing 0.6% Salcare SC60 dispersed in shampoo and applied on hair before and after rubbing by combing

| Capsules | Intensity Before Rubbing | Intensity After Rubbing |
|---|---|---|
| Control Capsule A | 2.0 | 4.1 |
| Capsule A | 2.4 | 5.6 |

The addition of only 0.1 wt % of polyquaternium-16 (Luviquat® FC550) to 0.6 wt % of poly(acrylamidopropyltrimonium chloride-co-acrylamide) (Salcare® SC60) improved significantly the performance of the microcapsules on hair. This result illustrates a better deposition of the microcapsules comprising a mixture of cationic copolymers.

Example 4

Application in Shampoo with 0.8% Cationic Copolymers

Capsules were assessed according to the protocol described in example 3 in shampoo base (Table 7). Results showed that the partial replacement of Salcare® 60 by polyquaternium-16 (Luviquat® FC550) improved the performance.

TABLE 9

Perfume intensity from microcapsules dispersed in shampoo and applied on hair, before and after rubbing by combing

| Capsules | Copolymers | Intensity Before Rubbing | Intensity After Rubbing |
|---|---|---|---|
| Comparative B | 0.8% Salcare SC60 | 1.3 | 2.6 |
| Capsule B | 0.6% Salcare SC60 0.2% Luviquat FC550 | 1.5 | 3.3 |

Example 5

Preparation of Polyurea-Based Microcapsules According to the Present Invention with poly(acrylamidopropyltrimonium chloride-co-acrylamide) (Salcare SC60) and Cassia hydroxypropyltrimonium chloride (Sensomer CT 250, Capsules E)

At least one polyisocyanate (e.g. Takenate® D-110N) was dissolved in a perfume oil (with Uvinul A Plus). The oil phase was then added to a biopolymer aqueous solution (e.g. 2% gum Arabic aqueous solution) and homogenized for 4 min using an Ultra-Turrax T25 disperser at 24000 rpm to form an O/W emulsion. The emulsion was pH adjusted to 10 using NaOH solution (counted as the aqueous phase). This emulsion was then stirred at 500 rpm using a mechanical overhead stirrer and optionally a reactant (e.g. a guanidine carbonate solution) was slowly added over 1 hour. Once the addition was complete, the reaction temperature was gradually elevated to 70° C. over 1 h and was maintained at 70° C. for 2 h before being allowed to cool to room temperature.

After 1.5 hours at 70° C., a cationic polymer was slowly added over 30 min. The reaction was then stirred for an additional 30 min at 70° C. before being allowed to cool to room temperature.

Microcapsules composition is reported in Table 10 below.

TABLE 10

Composition of capsules E

| Ingredient | Percentage |
|---|---|
| Perfume Oil[1] | 36.7 |
| Uvinul A Plus[2] | 1.9 |
| Takenate ® D-110N[3] | 4.9 |
| Guanidine Carbonate | 0.7 |
| Water | 8.0 |
| 2 wt % Gum Arabic Aqueous Solution | 47.0 |
| Cationic Polymer[4] | 0.8 |

[1]Perfuming composition from Table 11 below
[2]tracer for the quantification of oil deposition
[3]trimethylol propane adduct of xylylene diisocyanate; origin: Mitsui Chemicals, 75% polyisocyanate/25% ethyl acetate
[4]0.85% Salcare ® SC60 (poly(acrylamidopropyltrimonium chloride-co-acrylamide; origin BASF) + 0.15% Sensomer CT 250 (Cassia Hydroxypropyltrimonium Chloride Polymer)

TABLE 11

Perfume oil composition

| Ingredient | Parts |
|---|---|
| Isopropyl myristate | 0.3 |
| (Z)-3-hexen-1-ol butyrate | 0.6 |
| Delta damascone | 1.0 |
| 2,4-Dimethyl-3-cyclohexene-1-carbaldehyde | 1.0 |
| Habanolide ®[1] | 3.0 |
| Hedione ®[2] | 5.0 |
| Hexyl cinnamic aldehyde | 12.0 |
| Iso E Super ®[3] | 16.0 |
| Verdyl acetate | 24.0 |
| Lilial ®[4] | 37.0 |

[1]Trademark from Firmenich; pentadecenolide, origin: Firmenich SA, Geneva, Switzerland
[2]Trademark from Firmenich; Methyl-cis-3-oxo-2-pentyl-1-cyclopentane acetate, origin: Firmenich SA, Geneva, Switzerland
[3]Trademark from IFF; 7-acetyl, 1,2,3,4,5,6,7,8-octahydro-1,1,6,7-tetramethyl naphthalene
[4]Trademark from Givaudan; 3-(4-tert-butylphenyl)-2-methylpropanal Capsules E according to the invention were evaluated for deposition onto hair from a model surfactant mixture (Table 12) comparing the mixture of cationic polymers with control capsules wherein the blend has been replaced by single polymers. 1.0 wt % polymers were added to the Capsule E-type slurries for each respective polymer. The cationic polymer-coated capsule slurries were suspended into the model surfactant mixture 24 hours prior to deposition testing performed as described below.

Deposition Testing:

For the quantification of deposition, the following procedure was used. A 500 mg mini brown Caucasian hair swatch was wet with 40 mL of tap water (39° C.) aimed at the mount with a 140 mL syringe. The excess water was gently squeezed out once and 0.1 mL of a model surfactant mixture containing microcapsules loaded with a UV tracer (Uvinul A Plus) was applied with a 100 µL positive displacement pipet. The surfactant mixture was distributed with 10 horizontal and 10 vertical passes. The swatch was then rinsed with 100 mL of tap water (39° C.) with 50 mL applied to each side of the swatch aimed at the mount. The excess water was gently squeezed out and the hair swatch was then cut into a pre-weighed 20 mL scintillation vial. This process was repeated in triplicate and then the vials containing the cut hair were dried in a vacuum oven at 50-60° C. (100 Torr) for at least 5 hours. After the drying process, the vials were again weighed to determine the mass of the hair in the vials. Controls were also prepared by adding 0.1 mL of a model surfactant mixture containing microcapsules to an empty vial. 4 mL of 200 proof ethanol were then added to each vial and they were subjected to 60 min of sonication. After sonication, the samples were filtered through a 0.45 µm PTFE filter and analysed with a HPLC using a UV detector. To determine the percentage of deposition of microcapsules from a model surfactant mixture, the amount of Uvinul extracted from the hair samples was compared to the amount of Uvinul extracted from the control samples.

TABLE 12

Model Surfactant Mixture

| Ingredient | Actives Percentage |
|---|---|
| Sodium Laurel Ether Sulfate (SLES) | 12 |
| Cocamidopropyl Betaine (CAPB) | 3 |
| Salcare ® SC 60[1] Polymer | 0.5 |
| Water | 84 |
| Microcapsule Slurry (Equivalent Oil) | 0.5 |
| pH Adjustment (Citric Acid to pH 5.5) | *** |

[1]poly(acrylamidopropyltrimonium chloride-co-acrylamide; origin BASF

Deposition onto hair swatches was measured from this simplified model surfactant mixture which is meant to be representative of personal cleansing formulations such as shampoo or shower gel.

The results are presented in Table 13. The capsules according to the invention show greatest deposition enhancement due to synergy achieved by blending different polymers.

TABLE 13

Deposition results

| Cationic Polymer INCI Name | Supplier | Polymer-Supplier tradename | % Deposition |
|---|---|---|---|
| Polymer Blend | BASF/Lubrizol | BLEND (0.85% SC 60, 0.15% CT 250) | 19.9 |
| Cassia Hydroxypropyltrimonium Chloride Polymer | Lubrizol | Sensomer CT 250 | 1.7 |
| poly (acrylamidopropyltrimonium chloride-co-acrylamide | BASF | Salcare SC 60 | 17.1 |

Example 6

Application of Capsules E, F and H of Example 1 Prepared with 0.62% poly(acrylamidopropyltrimonium chloride-co-acrylamide) (Salcare® SC60) on Hair in Shampoo Base (Table 7 in Example 3)

Capsules E, F and H were dispersed in shampoo base (see table 7, example 3) and evaluated on hair by panelists. Comparative capsules C, E, F1, F2 and H in Example 2 were applied under the same conditions. Performance on hair was measured by sensory analysis as described in example 3.

Surprisingly, the performance of the capsules E, F and H increased with 0.62% of poly(acrylamidopropyltrimonium chloride-co-acrylamide) (Salcare® SC60) and only 0.1% of the second copolymer (Polyquaternium-7 or Polyquaternium 16).

TABLE 14

Sensory analysis of capsules E, F and H and comparative capsules C, E, F1, F2 and H on hair after application in shampoo

| Capsule | Intensity Before Rubbing | Intensity After Rubbing |
|---|---|---|
| Capsule E[1] | 3.7 | 6.3 |
| Capsule F[2] | 4.3 | 6.3 |
| Capsule H[3] | 4.0 | 6.5 |
| Comparative capsule C[4] | 3.7 | 5.4 |
| Comparative capsule E[5] | 1.7 | 2.1 |
| Comparative capsule F1[6] | 1.9 | 2.5 |
| Comparative capsule F2[7] | 2.5 | 4 |
| Comparative capsule H[8] | 2.7 | 3.4 |

[1] poly(acrylamidopropyltrimonium chloride-co-acrylamide) (Salcare ® SC60) + polyquaternium-16 (Luviquat FC550)
[2] poly(acrylamidopropyltrimonium chloride-co-acrylamide) (Salcare ® SC60) + polyquaternium-7 (Merquat 550)
[3] poly(acrylamidopropyltrimonium chloride-co-acrylamide) (Salcare ® SC60) + polyquaternium-16 (Luviquat Style)
[4] poly(acrylamidopropyltrimonium chloride-co-acrylamide) (Salcare ® SC60)
[5] polyquatemium-16 (Luviquat FC550)
[6] polyquatemium-7 (Merquat 550)
[7] polyquatemium-7 (Merquat 550)
[8] polyquatemium-16 (Luviquat Style)

The invention claimed is:

1. A core-shell microcapsule slurry comprising microcapsules having an oil-based core and a polymeric shell coated with a composition comprising at least a first cationic copolymer and a second cationic copolymer, wherein:
the weight ratio between the first copolymer and the second copolymer in the slurry is between 0.05 and 7; and
the first cationic copolymer comprises acrylamidopropyltrimonium chloride.

2. The microcapsule slurry according to claim 1, wherein the microcapsules are anionic.

3. The microcapsule slurry according to claim 1, wherein the second copolymer is selected from the group consisting of cationic polymers based on acrylamide, methacrylamide, N-vinylpyrrolidone, quaternized N,N-dimethylaminomethacrylate, diallyldimethylammonium chloride, quaternized vinylimidazole (3-methyl-1-vinyl-1H-imidazol-3-ium chloride), vinylpyrrolidone, cassia hydroxypropyltrimonium chloride, guar hydroxypropyltrimonium chloride, or polygalactomannan 2-hydroxypropyltrimethylammonium chloride ether, starch hydroxypropyltrimonium chloride, cellulose hydroxypropyltrimonium chloride, and mixtures thereof.

4. The microcapsule slurry according to claim 3, wherein the second copolymer is selected from the group consisting of polyquaternium-5, polyquaternium-6, polyquaternium-7, polyquaternium10, polyquaternium-11, polyquaternium-16, polyquaternium-22, polyquaternium-28, polyquaternium-43, polyquaternium-44, polyquaternium-46, cassia hydroxypropyltrimonium chloride, guar hydroxypropyltrimonium chloride, polygalactomannan 2-hydroxypropyltrimethylammonium chloride ether, starch hydroxypropyltrimonium chloride, cellulose hydroxypropyltrimonium chloride, and mixtures thereof.

5. The microcapsule slurry according to claim 1, wherein the first cationic copolymer consists of poly(acrylamidopropyltrimonium chloride-co-acrylamide).

6. The microcapsule slurry according to claim 3, wherein the second copolymer is selected from the group consisting of cationic polyacrylamide, polyquaternium-7, polyquaternium-16, cationic starch, cassia hydroxypropyltrimonium chloride, cationic cellulose and cationic polygalactomannan.

7. The microcapsule slurry according to claim 1, wherein the oil-based core comprises a perfume.

8. The microcapsule slurry according to claim 1, wherein the polymeric shell is selected from the group consisting of formaldehyde-free aminoplast, a polyurea-based polymeric shell, a polyurethane-based polymeric shell, and mixtures thereof.

9. A microcapsule powder obtained by drying the microcapsule slurry as defined in claim 1.

10. A process for the preparation of a core-shell microcapsule slurry as defined in claim 1, comprising the step of adding to an aqueous dispersion of un-coated microcapsules, a composition comprising at least a first cationic copolymer and a second cationic copolymer present in weight ratio comprised between 0.05 and 7, wherein the first cationic copolymer comprises acrylamidopropyltrimonium chloride.

11. The process according to claim 10, wherein the composition of at least a first and a second copolymers is added in an amount such that the total concentration of cationic copolymers is comprised between 0.3 and 1.5 wt % of the slurry.

12. The process according to claim 10, wherein the first cationic copolymer is present at a concentration comprised between 0.3 and 0.9 wt % of the microcapsule slurry.

13. The process according to claim 10, wherein the second cationic copolymer is present at a concentration comprised between 0.01 and 0.9 wt % of the microcapsule slurry.

14. A perfuming composition comprising
i) microcapsule slurry as defined in claim 7 or microcapsule powder as defined in claim 9 wherein the oil-based core comprises a perfume;
ii) at least one ingredient selected from the group consisting of a perfumery carrier and a perfuming co-ingredient;
iii) optionally perfumery adjuvant.

15. A consumer product in the form of a home- or personal-care product that includes a perfuming composition as defined in claim 14.

16. The consumer product of claim 15, in the form of a shampoo or hair-conditioner.

17. A shampoo or hair conditioner composition comprising
(i) from 1 to 50 wt % of surfactant
(ii) from 0.05 to 10 wt % of free perfume oil
(iii) from 0.05 to 10 wt % of an organic acid
(iv) from 0.2 to 0.8 wt % of a microcapsule slurry according to claim 1.

18. The perfuming composition according to claim 14, wherein the composition is used to deposit microcapsules on a substrate.

* * * * *